US00PP10200P

United States Patent [19]

Egger et al.

[11] Patent Number: Plant 10,200

[45] Date of Patent: Jan. 13, 1998

[54] ASIATIC HYBRID LILY PLANT NAMED 'CEB GOLDEN'

[75] Inventors: Donald L. Egger, Wilsonville; Edward A. McRae, Sandy, both of Oreg.

[73] Assignee: Cebeco Lilies, Inc., Aurora, Oreg.

[21] Appl. No.: 692,230

[22] Filed: Aug. 7, 1996

[51] Int. Cl.[6] ..... A01H 5/00

[52] U.S. Cl. ..... Plt./87.4

[58] Field of Search ..... Plt./87.4

*Primary Examiner*—James R. Feyrer

*Attorney, Agent, or Firm*—Klarquist Sparkman Campbell Leigh & Whinston, LLP

[57] ABSTRACT

A new and distinct Asiatic Lily Hybrid having large gold flowers with large gold buds on genetically dwarf stems with dense foliage excellent for pot plant production.

1 Drawing Sheet

BACKGROUND OF THE INVENTION

The present invention relates to a new and distinct cultivar of Lily hybrid referred to commercially as an upright Asiatic hybrid pot lily and given the cultivar name 'Ceb Golden'. This invention was developed by controlled breeding in Aurora, Oreg., using 8-81, a proprietary, non-released plant as the seed parent, and 9-81, another proprietary, non-released plant as the pollen parent.

This invention has not been observed under all possible environmental conditions. The phenotype may vary significantly with variations in environment such as temperature, light intensity, and day length, without, however, any variation in genotype. The following traits have been repeatedly observed and are determined to be the basic characteristics of this invention which in combination distinguish this lily as a new and distinct cultivar: 1) large flowers of a bright gold color with very few spots; 2) beautiful, large, gold colored buds; 3) genetically dwarf stems excellent for pot plant production; 4) very uniform growth habit; 5) good vigor; and 6) good, dense foliage. Bulbs of this plant may be precooled and forced out of season for uniform pot plant production. In addition, this new lily shows good disease tolerance.

This invention is best compared to 'Butter Pixie' (U.S. Plant Pat. No. 6,422). Compared to 'Butter Pixie', this invention has darker gold flowers, thicker and wider tepals, and darker gold buds. It is also earlier and shorter.

Asexual reproduction of this new variety has been accomplished at Cebeco Lilies, Inc , in Aurora, Oreg., by scaling and tissue culture. The resulting plants have shown that the above-mentioned unique features are stable and reproduce true to type in each successive propagation.

Figure 2:
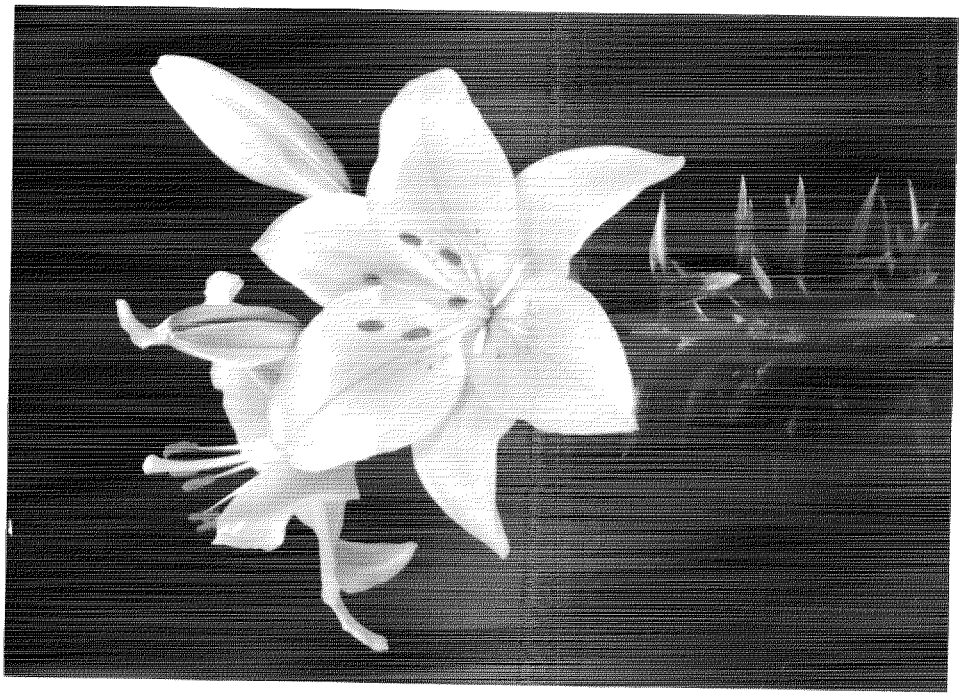
FIG. 2 is a photograph showing the 'Ceb Golden' lily.
Figure 1:
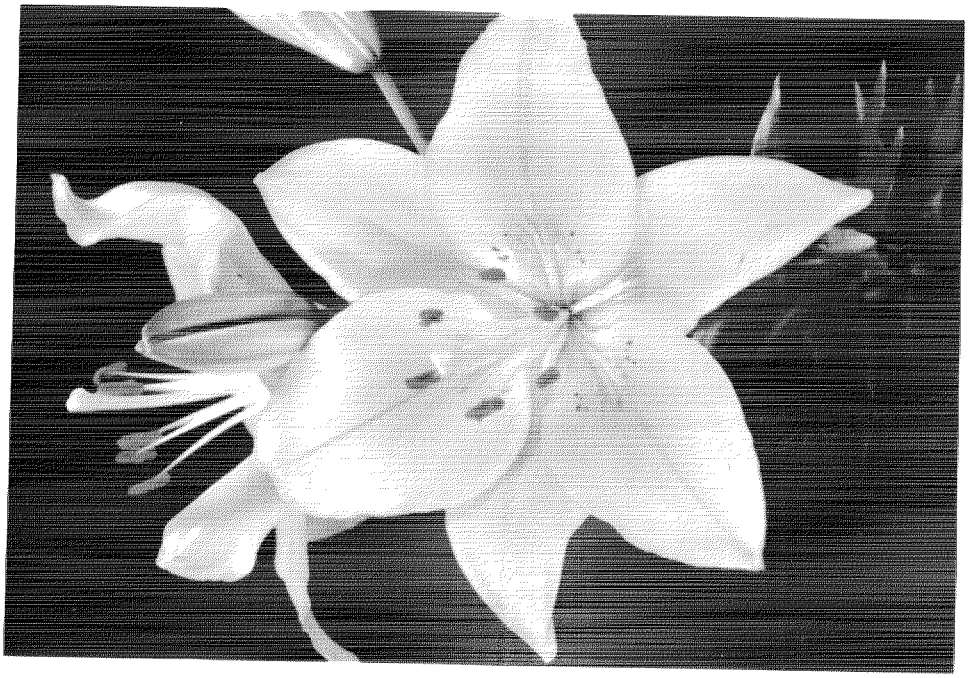
FIG. 1 is a close-up photograph which illustrates in greater detail a single flower of the new plant.

The photographs of the drawing were taken in June 1995 in a studio and illustrate the typical flower and foliage form, with color as true as reasonably possible in this type of color photograph.

DETAILED DESCRIPTION

The following is a detailed description of the invention based on plants produced under commercial practices in the Cebeco Lilies, Inc. fields in Aurora, Oreg. in June 1995.

Color references are made to The Royal Horticultural Society Colour Chart, except where the context indicates a term having its ordinary dictionary meaning.

THE PLANT

Origin: Seedling.

Parentage:

*Seed parent.*—8-81.

*Pollen parent.*—9-81.

Commercial classification: Hybrid Asiatic Lily, pot type.

Classification: Division I-AB, Semi-upright Asiatic Hybrid Lily, according to the Horticultural Classification of Lilies by The Royal Horticultural Society of London.

Form: Single erect stem bearing terminal cluster of flowers.

Height: About 30 cm. from the top of the soil to the top of the flowers from bulbs of 12–14 cm. in circumference.

Stem color: Yellow green (144A) with maroon spots (187B).

Growth habit: Vigorous, upright and rigid.

Internode length: About 1 to 5 mm.

Foliage:

*Arrangement.*—Spiral.

*Leaf size.*—To about 7.5 cm. long and 1.4 cm wide.

*Leaf shape.*—Lanceolate.

*Texture.*—Leathery.

*Aspect.*—Glossy.

*Color.*—Medium green on both sides. Closest to Yellow Green Group 147A.

Bulbs:

*Size.*—Variable, ranging to about 12–14 cm. in circumference as used commercially.

*Color.*—White.

THE BUD

Size: Large, to about 7 cm. long and 3 cm. wide just prior to opening.

Shape: Ovoid with an obtuse tip.

Rate of opening: The mature bud opens slowly in response to light.

Color: Dark Yellow. Yellow Group 13B.

THE FLOWER

Blooming habit: Annually, once and early season.

Days to bloom: Flowers approximately 60 days after spring greenhouse planting under typical commercial flower forcing conditions of 15 degrees Celsius night time temperatures.

Flower size: Medium-large.

Diameter: About 13 cm.

Depth: About 4 cm.
Borne: In an umbel or modified raceme of 4 flowers from bulbs 12 cm. in circumference.
Shape: When the flower first opens it is a flattened bowl shape. Later the shape flattens out more and the tepals reflex slightly at the tips.
Tepalage:
*Number.*—Six.
*Arrangement.*—Imbricated.
*Shape.*—Broadly ovate.
*Texture.*—Spongy, waxy, and thick.
*Aspect.*—Satiny.
*Size.*—Length: About 7.5 cm. Width: Inner tepals — about 50 mm. Outer tepals — about 36 mm.
Depth of imbrication: About 12 mm.
Nectary: About 2.5 cm. long; appear white but are yellow green with glandular pubescence; channels together on the bottom 1.4 cm.
Projections: Present as raised lines, some ending in white hairs and some in spots alongside the nectary.
Spots: On inner tepals only, 3–9 spots per tepal. Grayed-Purple Group 187A.
Blush: Orange. Above the nectary, Orange Group 24A.
Color:
*Topside.*—Gold. Yellow Group 13A. Blush and Midrib are orange. Orange Group 24A.
*Bottomside.*—Inner tepals — Yellow Group 13A. Outer tepals — Yellow Group 13 A on the edges with a duller orange along the midrib.
Discoloration: Slightly duller with age.
Fragrance: None.
Pedicle:
*Length.*—About 3–6 cm.
*Color.*—Yellow green (144A) overlaid with maroon spots, Grayed-Purple Group 187B.
Orientation: Ascending upwardly in a curve to about 45° from the horizontal.

THE REPRODUCTIVE ORGANS

Stamens:
*Number.*—Six, typical of the genus Lilium.
Anthers before dehiscence:
*Size.*—About 17 mm.
*Color.*—Light Brown. Greyed-Orange Group 165B.
Filaments:
*Length.*—About 50 mm.
*Color.*—Yellow. Yellow Group 6C-D.
Pollen:
*Color.*—Orange. Orange Group 24A.
Pistil:
*Number.*—One.
*Style.*—Length: About 48 mm. Color: Yellow. Yellow Group 12A lightening to Yellow Group 5B to 5C.
*Stigma.*—Color: Gold. Yellow Group 13A.

THE FRUIT

Fertility: Fertile.
Shape: Ovoid.
Color at maturity: Soft brown.

We claim:

1. A new and distinct cultivar of Asiatic hybrid lily plant substantially as herein shown and described.

* * * * *